United States Patent
LaVon et al.

(10) Patent No.: US 10,117,787 B2
(45) Date of Patent: Nov. 6, 2018

(54) METHODS AND APPARATUSES FOR TUCKING SIDE PANELS OF ABSORBENT ARTICLES

(71) Applicant: The Procter & Gamble Company, Cincinnati, OH (US)

(72) Inventors: Gary Dean LaVon, Liberty Township, OH (US); Uwe Schneider, Cincinnati, OH (US); Joseph Hung Lam, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 799 days.

(21) Appl. No.: 14/672,504

(22) Filed: Mar. 30, 2015

(65) Prior Publication Data
US 2015/0202093 A1    Jul. 23, 2015

Related U.S. Application Data

(62) Division of application No. 13/051,231, filed on Mar. 18, 2011, now Pat. No. 9,017,241.
(Continued)

(51) Int. Cl.
*B31F 1/08*        (2006.01)
*B31F 1/00*        (2006.01)
(Continued)

(52) U.S. Cl.
CPC .. *A61F 13/15747* (2013.01); *A61F 13/15764* (2013.01); *B65H 45/16* (2013.01)

(58) Field of Classification Search
CPC ......... A61F 13/15747; A61F 13/15764; B65H 45/16; B65H 45/164; B31F 1/08
(Continued)

(56) References Cited

U.S. PATENT DOCUMENTS 407,813 A    7/1889 Burdick
591,175 A   10/1897 Lorenz
(Continued)

FOREIGN PATENT DOCUMENTS

AU    78532/75        2/1975
EP    0 565 606 B1    3/1995
(Continued)

OTHER PUBLICATIONS

PCT International Search Report, dated Jul. 13, 2011, 9 pages.
(Continued)

*Primary Examiner* — Gloria R Weeks
(74) *Attorney, Agent, or Firm* — Charles R. Matson

(57) ABSTRACT

Aspects of the present disclosure relate to tucking opposing side panels into a chassis of a diaper pant. The apparatuses and methods may utilize one or more conveyors that advance the chassis along a machine direction. Each conveyor may have a vacuum zone that applies a vacuum force to hold the chassis. The chassis may be positioned between a first conveyor having a first vacuum zone and a second conveyor having a second vacuum zone. The conveyors may apply opposing vacuum forces to hold the first waist region apart from the second waist region while the chassis advances in the machine direction toward a tucking device. The vacuum forces are then removed from the waist regions as the tucking device pushes the side panels toward each other. Pushing the side panels toward each other causes the inner surfaces of the waist regions to simultaneously move toward each other.

10 Claims, 6 Drawing Sheets

Related U.S. Application Data

(60) Provisional application No. 61/322,349, filed on Apr. 9, 2010.

(51) Int. Cl.
*A61F 13/15* (2006.01)
*B65H 45/16* (2006.01)

(58) Field of Classification Search
USPC .......................................................... 469/405
See application file for complete search history.

(56) References Cited

U.S. PATENT DOCUMENTS

| | | | |
|---|---|---|---|
| 742,204 A | 10/1903 | Lorenz | |
| 795,046 A | 7/1905 | Lorenz | |
| 822,618 A | 6/1906 | Lorenz et al. | |
| 3,310,207 A | 3/1967 | Gore | |
| 3,848,594 A | 11/1974 | Buell | |
| 3,905,592 A | 9/1975 | Spencer et al. | |
| 3,929,135 A | 12/1975 | Thompson | |
| 3,994,486 A | 11/1976 | Nystrand | |
| 4,022,456 A | 5/1977 | Hooper et al. | |
| 4,316,756 A | 2/1982 | Wilson | |
| 4,324,246 A | 4/1982 | Mullane et al. | |
| 4,342,314 A | 8/1982 | Radel et al. | |
| 4,357,197 A | 11/1982 | Wilson | |
| 4,463,045 A | 7/1984 | Ahr et al. | |
| 4,501,587 A | 2/1985 | Enloe | |
| 4,609,518 A | 9/1986 | Curro et al. | |
| 4,610,678 A | 9/1986 | Weisman et al. | |
| 4,614,512 A | 9/1986 | Capdeboscq | |
| 4,629,643 A | 12/1986 | Curro et al. | |
| 4,662,875 A | 5/1987 | Hirotsu et al. | |
| 4,673,402 A | 6/1987 | Weisman et al. | |
| 4,694,978 A | 9/1987 | Westphal et al. | |
| 4,695,278 A | 9/1987 | Lawson | |
| 4,739,910 A | 4/1988 | Westphal et al. | |
| 4,795,454 A | 1/1989 | Dragoo | |
| 4,834,735 A | 5/1989 | Alemany et al. | |
| 4,846,815 A | 7/1989 | Scripps | |
| 4,888,231 A | 12/1989 | Angstadt | |
| 4,894,060 A | 1/1990 | Nestegard | |
| 4,940,464 A | 7/1990 | VanGompel et al. | |
| 4,946,527 A | 8/1990 | Battrell | |
| 4,963,140 A | 10/1990 | Robertson et al. | |
| 4,968,312 A | 11/1990 | Khan | |
| 4,988,344 A | 1/1991 | Reising et al. | |
| 4,988,345 A | 1/1991 | Reising | |
| 4,990,147 A | 2/1991 | Freeland | |
| 5,006,394 A | 4/1991 | Baird | |
| 5,062,840 A | 11/1991 | Holt et al. | |
| 5,092,861 A | 3/1992 | Nomura et al. | |
| 5,137,537 A | 8/1992 | Herron et al. | |
| 5,147,345 A | 9/1992 | Young et al. | |
| 5,151,092 A | 9/1992 | Buell et al. | |
| 5,167,897 A | 12/1992 | Weber et al. | |
| 5,171,236 A | 12/1992 | Dreier et al. | |
| 5,221,274 A | 6/1993 | Buell et al. | |
| 5,246,433 A | 9/1993 | Hasse et al. | |
| 5,260,345 A | 11/1993 | DesMarais et al. | |
| 5,269,755 A | 12/1993 | Bodicky | |
| 5,300,007 A | 4/1994 | Kober | |
| 5,306,266 A | 4/1994 | Freeland | |
| 5,342,338 A | 8/1994 | Roe | |
| 5,360,420 A | 11/1994 | Cook et al. | |
| 5,387,207 A | 2/1995 | Dyer et al. | |
| 5,397,318 A | 3/1995 | Dreier | |
| 5,514,121 A | 5/1996 | Roe et al. | |
| 5,540,671 A | 7/1996 | Dreier | |
| 5,554,142 A | 9/1996 | Dreier et al. | |
| 5,562,646 A | 10/1996 | Goldman et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,595,567 A | 1/1997 | King et al. | |
| 5,599,335 A | 2/1997 | Goldman et al. | |
| 5,624,427 A | 4/1997 | Bergman et al. | |
| 5,626,711 A | 5/1997 | Herrmann | |
| H1670 H | 7/1997 | Kirkpatrick et al. | |
| 5,643,588 A | 7/1997 | Roe et al. | |
| 5,650,222 A | 7/1997 | DesMarais et al. | |
| 5,653,703 A | 8/1997 | Roe et al. | |
| 5,669,894 A | 9/1997 | Goldman et al. | |
| 5,674,216 A | 10/1997 | Buell et al. | |
| 5,702,551 A | 12/1997 | Huber et al. | |
| 5,735,840 A | 4/1998 | Kline et al. | |
| 5,779,831 A | 7/1998 | Schmitz | |
| 5,788,805 A | 8/1998 | Herrmann | |
| 5,865,823 A | 2/1999 | Curro | |
| 5,873,870 A | 2/1999 | Seitz et al. | |
| 5,897,545 A | 4/1999 | Kline et al. | |
| 5,904,802 A | 5/1999 | Niedermeyer | |
| 5,928,212 A | 7/1999 | Kline et al. | |
| 5,934,523 A | 8/1999 | Willett et al. | |
| 5,941,864 A | 8/1999 | Roe | |
| 5,957,908 A | 9/1999 | Kline et al. | |
| 5,968,025 A | 10/1999 | Roe et al. | |
| 6,010,491 A | 1/2000 | Roe et al. | |
| 6,015,934 A | 1/2000 | Lee et al. | |
| 6,036,805 A | 3/2000 | McNichols | |
| 6,107,537 A | 8/2000 | Elder et al. | |
| 6,113,717 A | 9/2000 | Vogt et al. | |
| 6,118,041 A | 9/2000 | Roe et al. | |
| 6,120,487 A | 9/2000 | Ashton | |
| 6,120,489 A | 9/2000 | Johnson et al. | |
| 6,153,209 A | 11/2000 | Vega et al. | |
| 6,251,097 B1 | 6/2001 | Kline et al. | |
| 6,375,646 B1 | 4/2002 | Widlund et al. | |
| 6,410,129 B2 | 6/2002 | Zhang et al. | |
| 6,414,215 B1 | 7/2002 | Roe | |
| 6,426,444 B2 | 7/2002 | Roe et al. | |
| 6,432,098 B1 | 8/2002 | Kline et al. | |
| 6,441,266 B1 | 8/2002 | Dyer et al. | |
| 6,478,785 B1 | 11/2002 | Ashton et al. | |
| 6,482,191 B1 | 11/2002 | Roe et al. | |
| 6,497,032 B2 | 12/2002 | Maxton et al. | |
| 6,513,221 B2* | 2/2003 | Vogt ................. A61F 13/15756 156/200 |
| 6,562,017 B1 | 5/2003 | Nakaoka et al. | |
| 6,572,575 B1 | 6/2003 | Klenp et al. | |
| 6,572,598 B1 | 6/2003 | Ashton et al. | |
| 6,573,423 B1 | 6/2003 | Herrlein et al. | |
| 6,586,652 B1 | 7/2003 | Roe et al. | |
| 6,627,787 B1 | 9/2003 | Zhang et al. | |
| 6,723,035 B2* | 4/2004 | Franklin ........... A61F 13/15747 493/313 |
| 6,776,316 B2* | 8/2004 | Van Eperen ...... A61F 13/15747 223/37 |
| 6,825,393 B2 | 11/2004 | Roe et al. | |
| 6,861,571 B1 | 3/2005 | Roe et al. | |
| 6,888,143 B2 | 5/2005 | Vogt et al. | |
| 6,945,924 B2 | 9/2005 | Brizzi et al. | |
| 7,028,841 B2 | 4/2006 | Otsubo | |
| 7,156,939 B2* | 1/2007 | Vogt ................. A61F 13/15747 156/160 |
| 7,175,584 B2 | 2/2007 | Maxton et al. | |
| 7,195,586 B2 | 3/2007 | Yamamoto et al. | |
| 7,201,744 B2 | 4/2007 | Van Gompel et al. | |
| 7,270,631 B2* | 9/2007 | Franklin ........... A61F 13/15747 493/313 |
| 7,314,465 B2 | 1/2008 | Van Gompel et al. | |
| 7,318,798 B2 | 1/2008 | Yamamoto et al. | |
| 7,322,925 B2 | 1/2008 | Couillard et al. | |
| 7,335,150 B2 | 2/2008 | Coenen et al. | |
| 7,384,386 B2 | 6/2008 | Sosalla | |
| 7,387,148 B2 | 6/2008 | Vogt et al. | |
| 7,399,266 B2 | 7/2008 | Aiolfi et al. | |
| 8,002,689 B2 | 8/2011 | Whitten et al. | |
| 8,145,338 B2 | 3/2012 | Kent et al. | |
| 8,145,343 B2 | 3/2012 | DeBruler et al. | |
| 8,145,344 B2 | 3/2012 | DeBruler et al. | |
| 8,211,080 B2 | 7/2012 | Ruman et al. | |
| 8,361,045 B2 | 1/2013 | Thorson et al. | |

(56) References Cited

U.S. PATENT DOCUMENTS

| | | |
|---|---|---|
| 8,486,038 B2 | 6/2013 | McCabe |
| 8,495,784 B2 | 7/2013 | Steinhardt et al. |
| 8,496,637 B2 * | 7/2013 | Hundorf ............. A61F 13/5323 604/368 |
| 8,617,341 B2 | 12/2013 | Schneider |
| 8,870,732 B2 * | 10/2014 | Schneider ......... A61F 13/15747 493/416 |
| RE45,256 E | 11/2014 | Vogt et al. |
| 2002/0123730 A1 | 9/2002 | Popp et al. |
| 2003/0062113 A1 | 4/2003 | Van Eperen et al. |
| 2003/0062120 A1 | 4/2003 | Lehner et al. |
| 2003/0062121 A1 | 4/2003 | Franklin et al. |
| 2003/0083636 A1 | 5/2003 | Kuen et al. |
| 2003/0233082 A1 | 12/2003 | Kline et al. |
| 2004/0112518 A1 | 6/2004 | Rossier et al. |
| 2004/0162536 A1 | 8/2004 | Becker et al. |
| 2004/0167486 A1 | 8/2004 | Busam et al. |
| 2005/0107764 A1 | 5/2005 | Matsuda et al. |
| 2006/0218700 A1 | 10/2006 | Uda |
| 2007/0129230 A1 * | 6/2007 | Sosalla ............. A61F 13/15747 493/441 |
| 2007/0208318 A1 | 9/2007 | Loritz et al. |
| 2008/0083489 A1 | 4/2008 | Schneider et al. |
| 2009/0094941 A1 | 4/2009 | Burns et al. |
| 2009/0098995 A1 | 4/2009 | Burns et al. |
| 2010/0280472 A1 | 11/2010 | Takeuchi et al. |
| 2011/0019943 A1 | 1/2011 | Piraneo |
| 2011/0247199 A1 * | 10/2011 | LaVon ............. A61F 13/15585 29/650 |
| 2011/0247747 A1 | 10/2011 | Schneider et al. |
| 2011/0251038 A1 | 10/2011 | LaVon et al. |
| 2012/0065043 A1 | 3/2012 | Lam et al. |
| 2012/0150331 A1 | 6/2012 | DeBruler et al. |
| 2012/0150332 A1 | 6/2012 | DeBruler et al. |
| 2012/0150336 A1 | 6/2012 | Kent et al. |
| 2012/0152436 A1 | 6/2012 | Schneider |
| 2012/0157280 A1 | 6/2012 | Schneider |
| 2012/0157281 A1 * | 6/2012 | Schneider ......... A61F 13/15756 493/379 |
| 2012/0196732 A1 | 8/2012 | Castro et al. |
| 2012/0241078 A1 | 9/2012 | Schlinz et al. |
| 2012/0246915 A1 * | 10/2012 | LaVon .............. A61F 13/15772 29/650 |
| 2012/0273129 A1 | 11/2012 | Handziak |
| 2013/0072887 A1 * | 3/2013 | LaVon .................... A61F 13/49 604/368 |
| 2013/0130879 A1 * | 5/2013 | Schoon ............. A61F 13/15747 493/405 |
| 2013/0149925 A1 | 6/2013 | Handziak et al. |
| 2013/0160194 A1 | 6/2013 | Shimada |
| 2013/0269864 A1 | 10/2013 | McCabe |
| 2013/0277154 A1 | 10/2013 | Fritz et al. |
| 2013/0281957 A1 | 10/2013 | Fritz et al. |
| 2013/0296148 A1 | 11/2013 | Schneider et al. |
| 2013/0296149 A1 | 11/2013 | Schneider et al. |
| 2014/0031780 A1 | 1/2014 | Vogt et al. |
| 2014/0080692 A1 | 3/2014 | Lenser et al. |
| 2014/0378287 A1 | 12/2014 | Schneider et al. |

FOREIGN PATENT DOCUMENTS

| | | |
|---|---|---|
| EP | 1 639 908 A1 | 3/2006 |
| EP | 1 889 590 A2 | 2/2008 |
| EP | 1 429 704 B1 | 7/2010 |
| EP | 1 429 700 B1 | 8/2010 |
| FR | 2 209 368 | 6/1974 |
| FR | 2 219 636 | 9/1974 |
| GB | 2 245 149 | 1/1992 |
| JP | 4-828 B | 4/1990 |
| JP | 3021190 | 11/1995 |
| JP | 9-110019 A | 4/1997 |
| JP | 9-131364 A | 5/1997 |
| JP | 2003-250826 A | 9/2003 |
| JP | 2005-296 A | 1/2005 |
| WO | WO 93/25172 | 12/1993 |
| WO | WO 94/14395 | 7/1994 |
| WO | WO 95/16746 | 6/1995 |
| WO | WO 2006/015141 | 2/2006 |

OTHER PUBLICATIONS

All Office Actions, U.S. Appl. No. 13/051,231.
All Office Actions and Patent Board Decision, U.S. Appl. No. 14/479,424.
All Office Actions, U.S. Appl. No. 13/051,241.

* cited by examiner

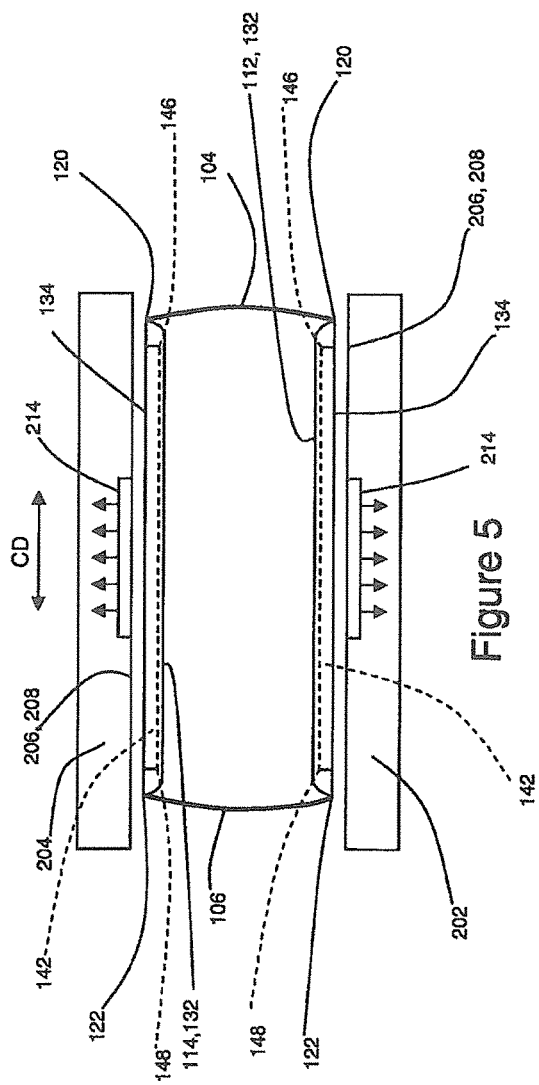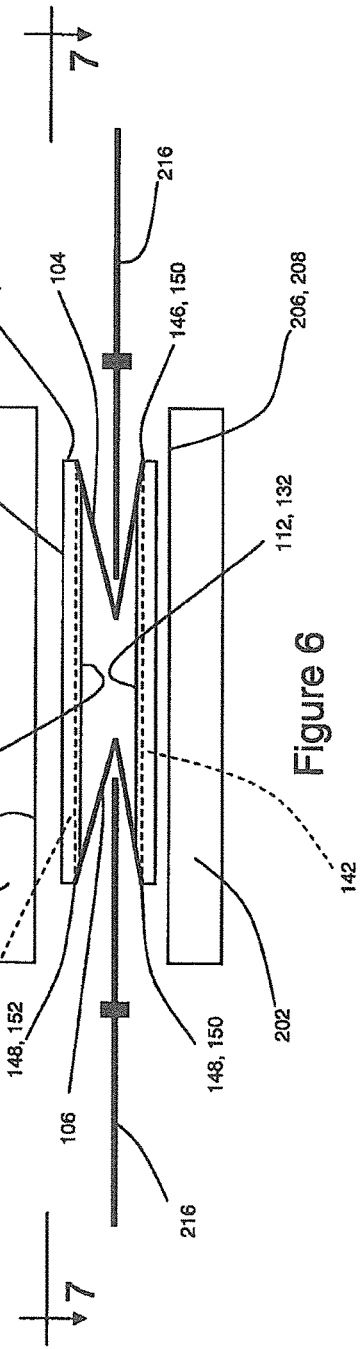

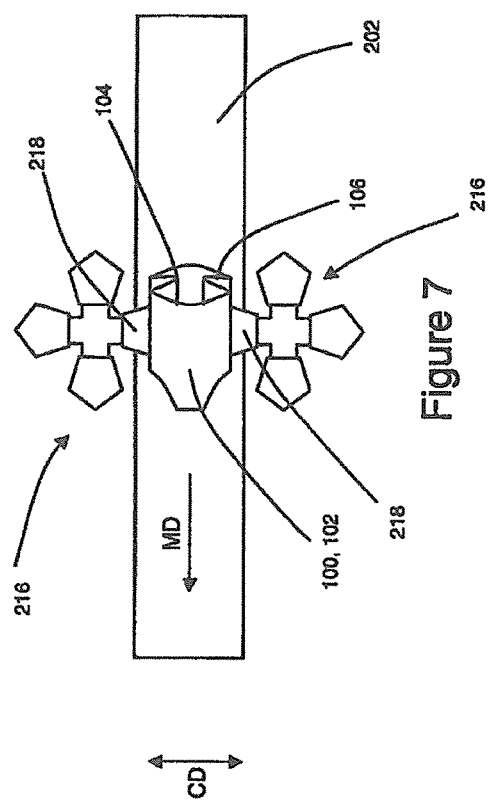
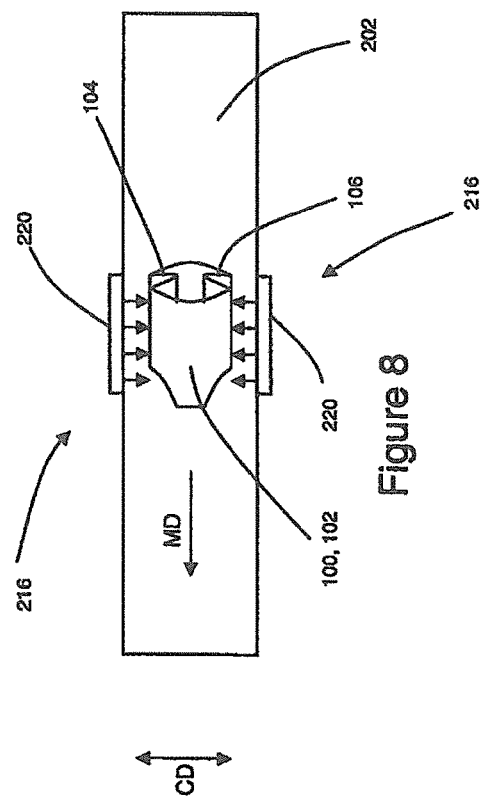

METHODS AND APPARATUSES FOR TUCKING SIDE PANELS OF ABSORBENT ARTICLES

CROSS REFERENCE TO RELATED APPLICATION

This application is a Divisional of U.S. application Ser. No. 13/051,231, filed on Mar. 18, 2011, which claims the benefit of U.S. Provisional Application No. 61/322,349, filed on Apr. 9, 2010, both of which are hereby incorporated by reference.

FIELD OF THE INVENTION

The present disclosure relates to methods and apparatuses for manufacturing absorbent articles, and more particularly, methods and apparatuses for tucking side panels of diaper pants.

BACKGROUND OF THE INVENTION

Along an assembly line, various types of articles, such as for example, diapers and other absorbent articles, may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Webs of material and component parts used to manufacture diapers may include: backsheets, topsheets, leg cuffs, waist caps, absorbent core components, front and/or back ears, fastener components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

After the final knife cut, absorbent articles may also undergo a folding process prior to packaging. Diaper pants may also include additional manufacturing steps not used in the manufacture of conventional taped diapers. For example, diaper pants may include side panels that connect front and rear waist regions with each other. Thus, after being folded into a U about a lateral centerline in the same or similar way as conventional diapers, the side panels on diaper pants may connect the front and rear waist regions to form a waist opening and a pair of leg openings. In addition, the side panels may be laterally tucked inside the diaper pants before packaging.

Some currently available side panel tucker processes advance the diaper pant in a machine direction between upper and lower vacuum conveyors. In such configurations, the upper vacuum conveyor may apply an upward vacuum force to the front waist region of the diaper pant while the lower vacuum conveyor may apply a downward vacuum force to the rear waist region of the diaper pant. As such, the opposing vacuum forces hold the waist regions of the diaper pant apart from each other. Then, while the waist regions of the diaper are held apart by vacuum, a rotating tucker blade or air stream may be used to push the side panels into the interior of the diaper. Once the side panels are tucked into the diaper, the front and rear waist regions are then pressed against each other to hold the side panels in the tucked position. However, forces exerted on the diaper as a result of the vacuum and the relatively high travel speeds in combination with elasticity of the side panels, may result in the side panels unintentionally moving back out of the diaper before the front and rear waist regions are pressed against each other.

SUMMARY OF THE INVENTION

Aspects of the present disclosure relate to apparatuses and methods for tucking first and second opposing side panels into a chassis of a diaper pant.

In one form, a method may be configured for tucking first and second opposing side panels into a chassis of a diaper pant, wherein the chassis includes an inner surface and an outer surface, the chassis having longitudinally opposing first and second waist regions, longitudinally opposing first and second waist end edges disposed in the first and second waist regions, and a crotch region longitudinally intermediate of the first and second waist regions, the first and second side panels connecting the first waist region with the second waist region to form a waist opening and a pair of leg openings. The method may include the steps of: positioning the chassis between a first conveyor having a first vacuum zone and a second conveyor having a second vacuum zone; applying a first vacuum force from the first vacuum zone to the first waist region and applying a second vacuum force from the second vacuum zone to the second waist region; holding the first waist region of the chassis apart from the second waist region of the chassis using opposing vacuum forces from the first and second vacuum zones; advancing the chassis in a machine direction with the first and second conveyors; removing the first vacuum force from the first waist region and removing the second vacuum force from the second waist region; and pushing the first side panel and the second side panel a distance laterally inward toward each other while the first vacuum force and the second vacuum force are removed from the first and second waist regions.

In another form, a method may be configured for tucking first and second opposing side panels into a chassis of a diaper pant, wherein the chassis includes an inner surface and an outer surface, the chassis having longitudinally opposing first and second waist regions, longitudinally opposing first and second waist end edges disposed in the first and second waist regions, and a crotch region longitudinally intermediate of the first and second waist regions, the first and second side panels connecting the first waist region with the second waist region to form a waist opening and a pair of leg openings. The method may include the steps of: positioning the chassis on a conveyor having a vacuum zone; applying a vacuum force from the vacuum zone to the first waist region of the chassis; holding the first waist region and the second waist region of the chassis apart using opposing vacuum forces from first and second vacuum zones; advancing the chassis in a machine direction with the conveyor; removing the vacuum force from the first waist region; and moving the inner surface of the chassis in the first waist region and the second waist region toward each other by pushing the first side panel and the second side panel laterally inward toward each other while the vacuum force is removed from the first waist region.

BRIEF DESCRIPTION OF THE DRAWINGS

FIG. 5 shows a cross-sectional view of the apparatus and a diaper pant of FIG. 4 taken along line 5-5.

FIG. 6 shows a cross-sectional view of the apparatus and a diaper pant of FIG. 4 taken along line 6-6.

FIG. 7 shows a cross-sectional view of a tucking apparatus utilizing rotating tucker blades and diaper pant of FIG. 6 taken along line 7-7.

FIG. 8 show a cross-sectional view of a tucking apparatus utilizing air jets and diaper pant of FIG. 6 taken along line 7-7.

DETAILED DESCRIPTION OF THE INVENTION

Figure 1:
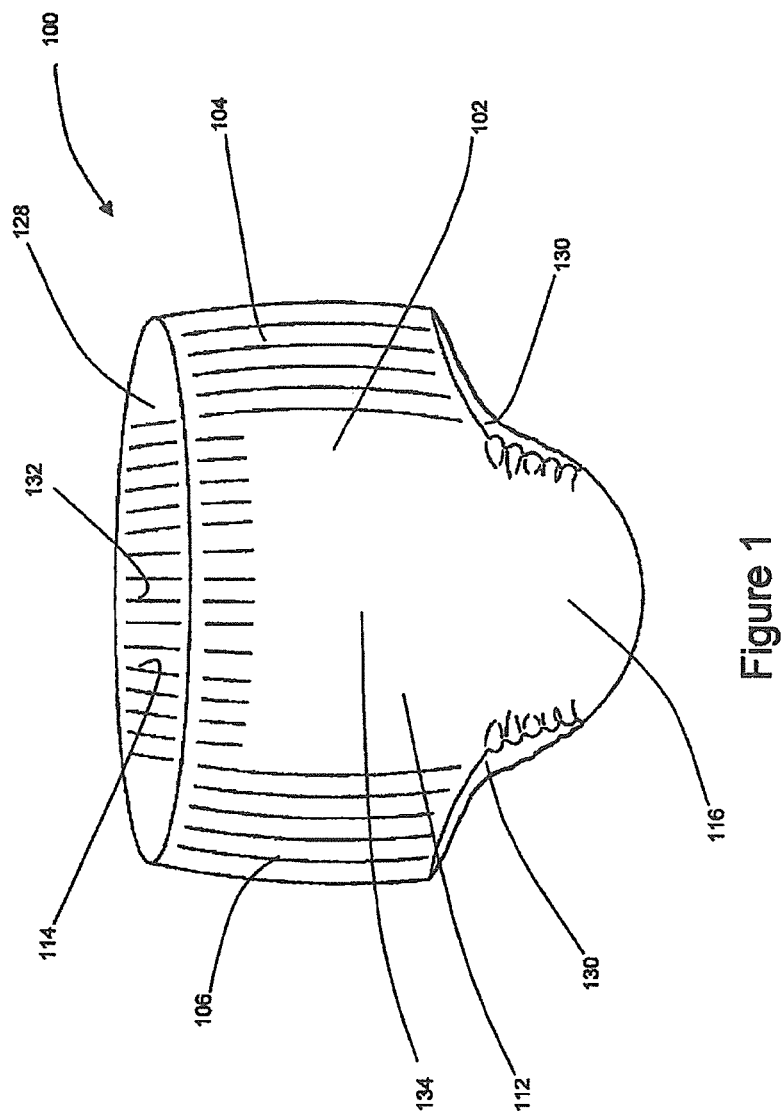
FIG. 1 is a perspective view a diaper pant.

The following term explanations may be useful in understanding the present disclosure:

"Absorbent article" is used herein to refer to consumer products whose primary function is to absorb and retain soils and wastes. Non-limiting examples of absorbent articles include diapers, training pants, pull-on pant-type diapers, refastenable diapers or pant-type diapers, incontinence briefs and undergarments, diaper holders and liners, feminine hygiene garments such as panty liners, absorbent inserts, and the like.

"Diaper" is used herein to refer to an absorbent article generally worn by infants and incontinent persons about the lower torso.

"Bi-fold" means the leading edge portion and the trailing edge portion of an article on a production line are brought together in a face-to-face configuration once the article is folded about a fold line extending laterally across the article as the article moves in the machine direction of travel.

The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "disposed" is used herein to mean that an element(s) is formed (joined and positioned) in a particular place or position as a macro-unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "taped diaper" (also referred to as "open diaper") refers to disposable absorbent articles having an initial front waist region and an initial back waist region that are not fastened, pre-fastened, or connected to each other as packaged, prior to being applied to the wearer.

Aspects of the present disclosure involve methods and apparatuses for manufacturing articles, and more particularly, apparatuses and methods for tucking first and second laterally opposing side panels into a chassis of a diaper pant. As discussed in more detail below, embodiments of the apparatuses and methods disclosed herein may utilize one or more conveyors that advance the chassis along a machine direction. Each conveyor may have a vacuum zone that applies a vacuum force to hold the chassis of the diaper. In some embodiments, the chassis is positioned between a first conveyor having a first vacuum zone and a second conveyor having a second vacuum zone. The conveyors may apply a first vacuum force from the first vacuum zone to the first waist region and may apply a second vacuum force from the second vacuum zone to the second waist region. As such, the opposing vacuum forces hold the first waist region of the chassis apart from the second waist region of the chassis while the chassis advances in the machine direction toward a tucking device. The vacuum forces are then removed from the waist regions as the tucking device pushes the side panels toward each other. Pushing the side panels toward each other while the vacuum forces are removed causes the inner surfaces of the first waist region and the second waist region to simultaneously move toward each other. In some embodiments, one waist region may continue to be held with a vacuum zone while the tucking device pushes the side panels, causing the inner surface of the other waist region to simultaneously move toward the waist region held by vacuum force. With the side panels tucked into the chassis, the front and rear waist regions are pressed against each other to maintain the side panels in the tucked position.

The following provides a description of diaper pants and associated components to help provide additional context to the subsequent discussion of side panel tucking methods and apparatuses.

The terms "diaper pant" and "pant" (also referred to as "training pant," "pre-closed diaper," "pant diaper," and "pull-on diaper") refers herein to disposable absorbent articles having a continuous perimeter waist opening and laterally opposing continuous perimeter leg openings designed for infant or adult wearers. A pant can be configured with a continuous or closed waist opening and at least one continuous, closed, leg opening as packaged, prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed or combinations thereof). Example pants are disclosed in various configurations are disclosed in U.S. Pat. Nos. 5,246,433; 5,569,234; 6,120,487; 6,120,489;

4,940,464; 5,092,861; 5,897,545; 5,957,908; 6,036,805; 6,113,717; and U.S. Patent Publication No. 2003/0233082.

Figure 2:
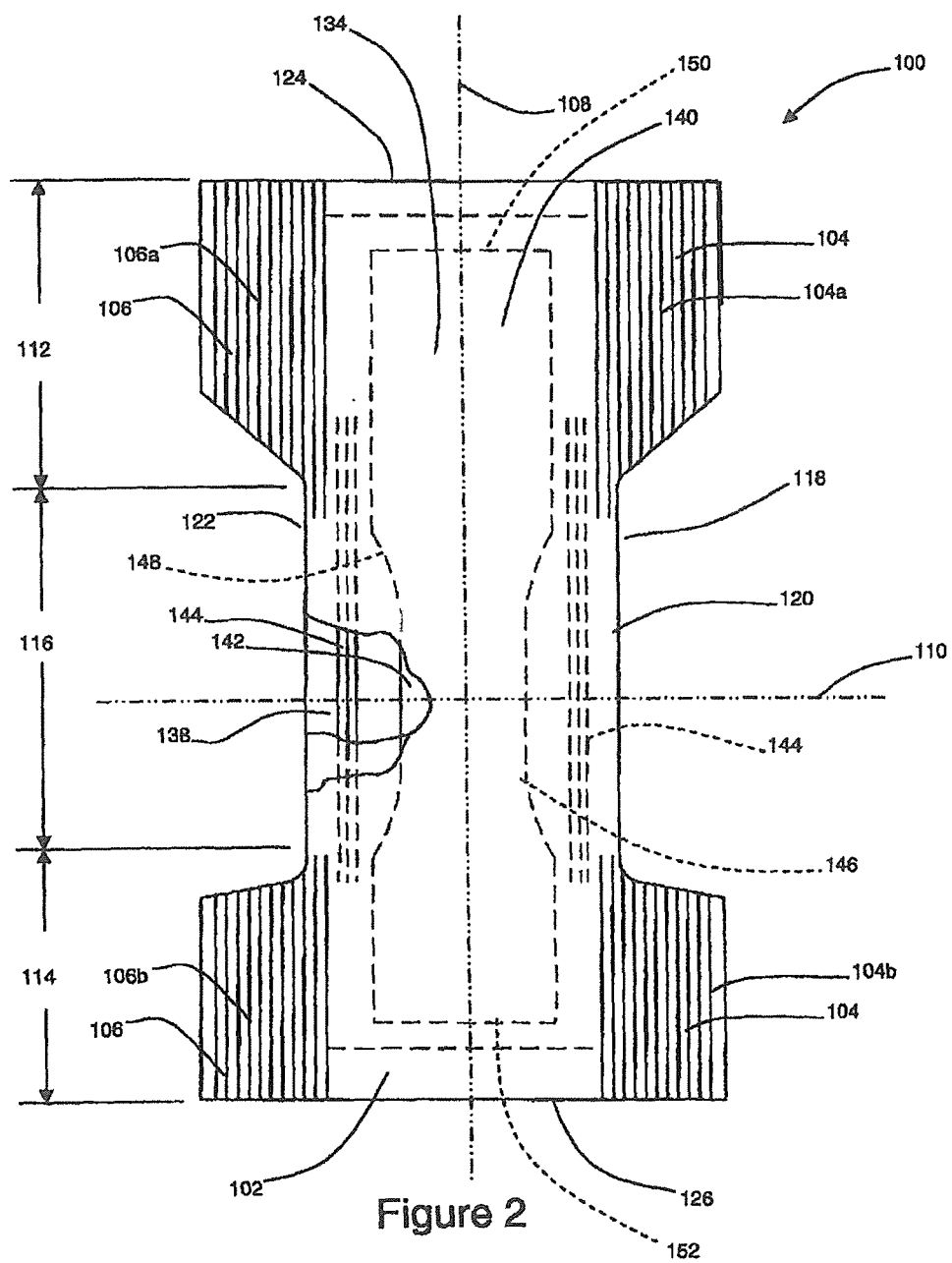
FIG. 2 is a partially cut away plan view of the diaper pant shown in FIG. 1.
Figure 3:
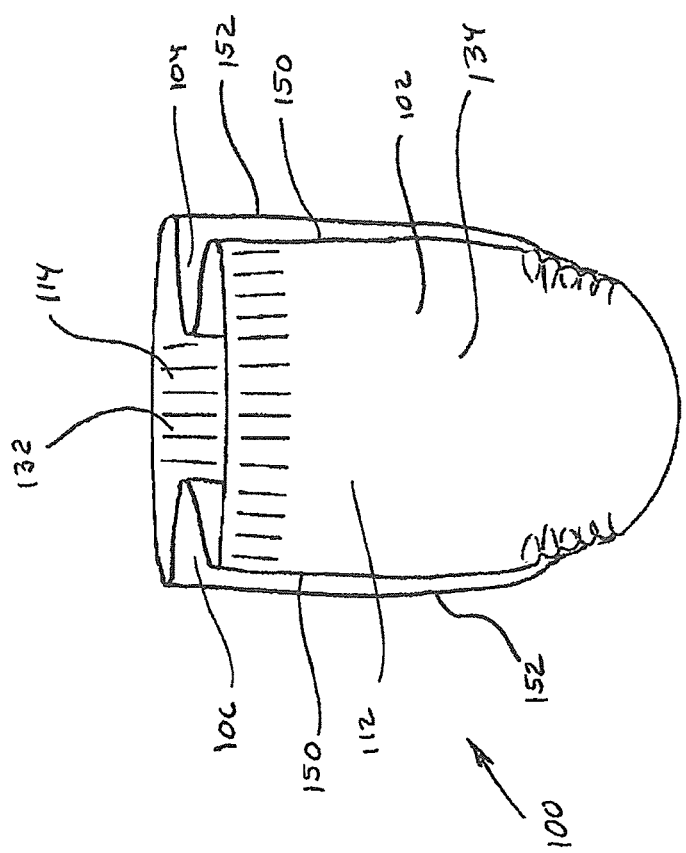
FIG. 3 is a perspective view of the diaper pant of FIG. 1 with side panels tucked into the interior of a chassis.

For the purposes of a specific illustration, FIG. 1 shows one example of a plan view of a diaper pant 100 including a chassis 102 and opposing first and second side panels 104, 106. FIG. 2 shows the diaper pant 100 in a flat, unfolded condition, with the portion of the diaper that faces away from a wearer oriented towards the viewer. A portion of the chassis structure is cut-away in FIG. 2 to more clearly show the construction of and various features that may be included in embodiments of the diaper pant 100. FIG. 3 shows the diaper pant 100 of FIG. 1 with opposing side panels tucked into the chassis 102.

To provide a frame of reference for the present discussion, the chassis 102 is shown with a longitudinal axis 108 and a lateral axis 110. The chassis 102 is shown as having a first waist region 112, a second waist region 114, and a crotch region 116 disposed intermediate the first and second waist regions. The periphery of the chassis 118 is defined by a first longitudinal side edge 120, a second longitudinal side edge 122; a first waist end edge 124 disposed in the first waist region 112; and a second waist end edge 126 disposed in the second waist region 114. As shown in FIG. 1, the first and second side panels 104, 106 connect the first waist region 112 with the second waist region 114 of the chassis 102 to form a waist opening 128 and two leg openings 130.

As shown in FIGS. 1 and 2, the chassis includes an inner, body facing surface 132, and an outer, garment facing surface 134. As shown in FIG. 2, the chassis 102 may include a topsheet 138 forming a portion of the body facing surface 132. The chassis 102 may also include a backsheet 140 formed from a laminate including an outer covering layer and an inner layer. An absorbent core 142 may be disposed between a portion of the topsheet 138 and the backsheet 140. The chassis 102 may also include leg elastics 144, such as shown in FIG. 2, and an elastic waist region to enhance the fit around the legs and waist of the wearer. Example leg elastic and leg cuff embodiments are disclosed in, for example, U.S. Pat. Nos. 4,695,278 and 4,795,454. It is to be appreciated that any one or more of the regions of the chassis may be stretchable and may include various types of elastomeric materials and/or laminates. As such, the diaper may be configured to adapt to a specific wearer's anatomy upon application and to maintain contact with the wearer's anatomy during wear.

As previously mentioned, the chassis 102 may include a backsheet 140, shown for example, in FIG. 2. The backsheet may also define the outer surface 134 of the chassis 102. In some embodiments, the backsheet may be configured to prevent exudates absorbed and contained within the chassis from soiling articles that may contact the diaper, such as bedsheets and undergarments. Certain backsheet embodiments may be fluid permeable, while other embodiments may be impervious to liquids (e.g., urine) and include a thin plastic film. Some backsheet films may include those manufactured by Tredegar Industries Inc. of Terre Haute, Ind. and sold under the trade names X15306, X10962, and X10964. Other backsheet materials may include breathable materials that permit vapors to escape from the diaper while still preventing exudates from passing through the backsheet. Exemplary breathable materials may include materials such as woven webs, nonwoven webs, composite materials such as film-coated nonwoven webs, monolithic films and microporous films. Example breathable composite materials are described in greater detail in PCT Application No. WO 95/16746 and U.S. Pat. No. 5,865,823, both of which are hereby incorporated by reference. Other breathable backsheets including nonwoven webs and apertured formed films are described in U.S. Pat. Nos. 5,571,096 and 6,573, 423, which are both hereby incorporated by reference.

The backsheet 140 may be formed by only one sheet (or layer) material such as a breathable (or microporous or monolithic) film material or a non-breathable (or non-microporous) film material. In some embodiments, the backsheet may be formed by two (or more) sheet (or layer) materials which may include a non-breathable (or breathable) film material and a nonwoven outer cover material. In some embodiments, the backsheet may be formed by a laminate of two sheet (or layer) materials joined together, for example, the backsheet may include a non-breathable film material forming the inner layer of the backsheet and a nonwoven material forming the outer layer which may be joined to the garment facing surface of the film material to provide a cloth-like and/or garment-like feel. In accordance with the discussion above, graphics may be printed on the film, the nonwoven, or the composite substrate to make printed component material, which may be converted into absorbent articles comprising printed backsheets.

As previously mentioned, the chassis 102 may include a topsheet 138, shown for example, in FIG. 2. The topsheet 138 may also define a portion of the inner surface 132 of the chassis 102. All or a portion of the topsheet may be liquid pervious, permitting liquid to readily penetrate there through. As such, the topsheet may be manufactured from a wide range of materials, such as porous foams; reticulated foams; apertured nonwovens or plastic films; or woven or nonwoven webs of natural fibers (e.g., wood or cotton fibers), synthetic fibers (e.g., polyester or polypropylene fibers), or a combination of natural and synthetic fibers. One example of a topsheet including a web of staple length polypropylene fibers is manufactured by Veratec, Inc., a Division of International Paper Company, of Walpole, Mass. under the designation P-8. Examples of formed film topsheets are described in U.S. Pat. Nos. 3,929,135; 4,324,246; 4,342,314; 4,463,045; and 5,006,394, all of which are hereby incorporated by reference herein. Other topsheets may be made in accordance with U.S. Pat. Nos. 4,609,518 and 4,629,643, both of which are hereby incorporated by reference.

In some embodiments, the topsheet is made of a hydrophobic material or is treated to be hydrophobic in order to isolate the wearer's skin from liquids contained in the absorbent core. If the topsheet is made of a hydrophobic material, at least the upper surface of the topsheet may be treated to be hydrophilic so that liquids will transfer through the topsheet more rapidly. The topsheet can be rendered hydrophilic by treating it with a surfactant or by incorporating a surfactant into the topsheet. A more detailed discussion of such a treatment and hydrophilicity is contained in U.S. Pat. Nos. 4,988,344 and 4,988,345, both of which are hereby incorporated by reference. A more detailed discussion of some methods for incorporating surfactant in the topsheet can be found in U.S. Statutory Invention Registration No. H1670, which was published on Jul. 1, 1997, in the names of Aziz et al., all of which are hereby incorporated by reference. In some embodiments, the topsheet 138 may include an apertured web or film that is hydrophobic. This may be accomplished eliminating the hydrophilizing treatment step from the production process and/or applying a hydrophobic treatment to the topsheet, such as a polytetrafluoroethylene compound like SCOTCHGUARD or a hydrophobic lotion composition, as described below. A more detailed discussion of various apertured topsheets can be found in U.S. Pat. Nos. 5,342,338; 5,941,864; 6,010,491; and 6,414,215, all of which are hereby incorporated by referenced.

As previously mentioned, the chassis 102 may also include an absorbent core 142. As shown for example in FIG. 2, the absorbent core 142 may include a first longitudinal side edge 146 laterally separated from a second longitudinal side edge 148, and a first end edge 150 longitudinally separated from a second end edge 152. The absorbent core may also include components such as an acquisition layer and absorbent material that is generally compressible, conformable, non-irritating to the wearer's skin and capable of absorbing and retaining liquids such as urine and other body exudates. The absorbent core can also be manufactured in a wide variety of sizes and shapes (e.g., rectangular, hourglass, T-shaped, asymmetric, etc.). The absorbent core may also include a wide variety of liquid-absorbent materials commonly used in disposable diapers and other absorbent articles. In one example, the absorbent core includes comminuted wood pulp, which is generally referred to as airfelt. Examples of other absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

It is to be appreciated that the configuration and construction of the absorbent core may be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). Exemplary absorbent structures are described in U.S. Pat. Nos. 4,610,678; 4,673,402; 4,834,735; 4,888,231; 5,137,537; 5,147,345; 5,342,338; 5,260,345; 5,387,207; and 5,650,222, all of which are hereby incorporated by reference.

The absorbent core may also have a multiple layered construction. A more detailed discussion of various types of multi-layered absorbent cores can be found in U.S. Pat. Publication Nos. 2004/0162536A1 and 2004/0167486A1; U.S. Pat. Nos. 5,669,894; 6,441,266; 5,562,646; European Pat. No. EP0565606B1; PCT Publication No. WO 2006/015141, which are all hereby incorporated by reference. In some embodiments, the diaper pant includes an absorbent core that is stretchable. In such a configuration, the absorbent core may be adapted to extend along with other materials of the chassis in longitudinal and/or lateral directions. The absorbent core can also be connected with the other components of the chassis various ways. For example, the diaper may include a "floating core" configuration or a "bucket" configuration wherein the diaper includes an anchoring system that can be configured to counteract the forces tending to move the article on the wearer. Such an anchoring system can also be configured to anchor itself to a body of a wearer by contacting various parts of the body. In this way, the anchoring system can balance the collected moving forces with holding forces obtained from the anchoring. By balancing the collected moving forces with the obtained holding forces, the anchoring system can at least assist in holding the disposable wearable absorbent article in place on a wearer.

Embodiments of the diaper pant may also include pockets for receiving and containing waste, spacers which provide voids for waste, barriers for limiting the movement of waste in the article, compartments or voids which accept and contain waste materials deposited in the diaper, and the like, or any combinations thereof. Examples of pockets and spacers for use in absorbent products are described in U.S. Pat. Nos. 5,514,121; 5,171,236; 5,306,266; 5,397,318; 5,540,671; and PCT Application WO 93/25172; which are all hereby incorporated by reference. Examples of compartments or voids are disclosed in U.S. Pat. Nos. 4,968,312; 4,990,147; 5,062,840; 6,482,191; and 5,269,755, which are all hereby incorporated by reference. Examples of transverse barriers are described in U.S. Pat. Nos. 5,554,142 and 5,653,703; and PCT Patent Publication WO 94/14395, which are all hereby incorporated by reference. In addition to or in place of the voids, pockets and barriers, described above, embodiments of the absorbent article may also include a waste management element capable of effectively and efficiently accepting, storing and/or immobilizing viscous fluid bodily waste, such as runny feces, such as described in U.S. Pat. No. 6,010,491, which is hereby incorporated by reference.

As previously mentioned with reference to FIG. 1, embodiments of the diaper pant 100 may include first and second side panels 104, 106 that connect the first waist region 112 with the second waist region 114 of the chassis 102 to form the waist opening 128 and two leg openings 130. As shown in FIGS. 1 and 2, the first side panel 104 includes a first ear panel 104a connected with a second ear panel 104b, and the second side panel 106 includes a first ear panel 106a connected with a second ear panel 106b. The first ear panels 104a, 106a each include proximal regions connected with the first waist region 112 of the chassis 102. And second first ear panels 104b, 106b each include proximal regions connected with the second waist region 114 of the chassis 102. Distal regions of the first ear panel 104a and the second ear panel 104b may be connected or fastened to each other to form the first side panel 104, and distal regions of the first ear panel 106a and the second ear panel 106b may be connected or fastened to each other to form the second side panel 106. Although the side panels shown in FIGS. 1 and 2 are formed by connecting ear panels together, it is to be appreciated that the side panels may be of a single unitary piece construction. It should be appreciated that the side panels may also be formed as continuous extensions of one or both the first and second waist regions of the chassis. It is also to be appreciated that embodiments of the diaper pant that may be used with the methods and apparatuses herein may include various different types and configurations of side panels than those shown and described herein. Examples of various types of side panels are disclosed in U.S. Pat. Nos. 5,246,433; 5,569,234; 6,120,487; 6,120,489; 4,940,464; 5,092,861; 5,897,545; 5,957,908; 6,036,805; 6,113,717; and U.S. Patent Publication No. 2003/0233082, all of which are incorporated herein by reference.

It is to be appreciated that the proximal regions of the ear panels may be connected with the chassis in various ways, and the distal regions of the ear panels may be connected with each other in various ways. For example, the proximal regions and/or distal regions of the side panels may be permanently bonded, releasably connected, and/or refastenably connected with the chassis and/or each other, with for example, adhesives, cohesives, thermal bonding, ultrasonic bonding, mechanical bonding and mechanical fastening, e.g. hook and loop type fasteners. For example, one or more fastener elements may be located on the side panels and may be adapted to refastenably connect with one or more corresponding fastening elements located in the first or second waist regions or alternatively the fastener elements may be adapted to refastenably connect with one or more components of the absorbent article including the side panels. The diaper pants can also include other features such as elastically extensible side panels that may each include one or more pieces of material.

Depending on the particular configuration, it is to be appreciated that various types of fastening elements may be used with the diaper pant. In one example, the fastening elements include hook & loop fasteners, such as those available from 3M or Velcro Industries. In other examples, the fastening elements include adhesives and/or tap tabs, while others are configured as a macrofastener or hook (e.g., a MACRO or "button-like" fastener). Some exemplary fastening elements and systems are disclosed in U.S. Pat. Nos. 3,848,594; 4,662,875; 4,846,815; 4,894,060; 4,946,527; 5,151,092; and 5,221,274, which are all hereby incorporated by reference. Additional examples of fasteners and/or fastening elements are discussed in U.S. Pat. Nos. 6,482,191; 6,251,097; and 6,432,098, which are all hereby incorporated by reference. Other fastening systems are described in more detail in U.S. Pat. Nos. 5,595,567; 5,624,427; 5,735,840; and 5,928,212, which are all hereby incorporated by reference. The fastening system may also provide a means for holding the article in a disposal configuration as disclosed in U.S. Pat. No. 4,963,140, which is hereby incorporated by reference.

As previously mentioned, the apparatuses and methods according to the present disclosure may be utilized to tuck first and second opposing side panels 104, 106 into the chassis 102 of the diaper pant 100. FIG. 1 shows a diaper pant 100 with the first and second side panels 104, 106 in an untucked configuration, and FIG. 3 shows the diaper pant 100 with opposing side panels 104, 106 tucked into the chassis 102. As shown in FIG. 3, portions of each side panel 104, 106 inserted into the chassis 102 of the diaper pant 100 such that portions of the side panels are disposed between the interior surface 132 of the first waist region 112 and the second waist region 114. In addition, the insertion of the side panels 104, 106 into the chassis 102 defines first longitudinal fold lines 150 along the first waist region 112 and second longitudinal fold lines 152 along the second waist region 114.

Figure 4:
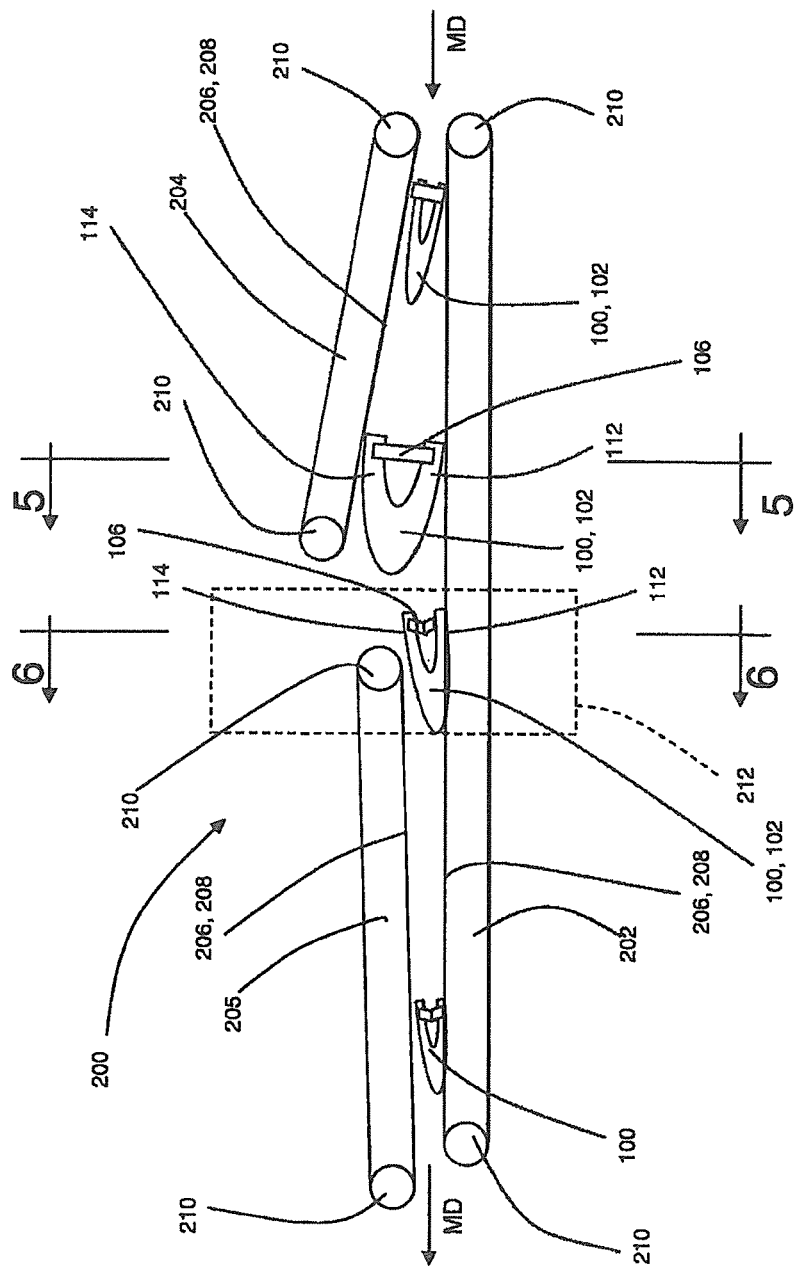
FIG. 4 is a schematic side view of diaper pants traveling in a machine direction along a side panel tucking apparatus.

FIG. 4 shows an embodiment of an apparatus 200 for tucking side panels 104, 106 into the chassis 102. The apparatus 200 can include a first conveyance 202, a second conveyance 204, and a third conveyance 205. Each conveyance 202, 204, 205 may be in the form of a conveyor and include a movable surface 206 that may be in the form of a belt 208 wrapped around rollers 210 and configured in an endless loop. One or more of the belts 208 may also be configured as a movable foraminous vacuum conveyor belt that exerts vacuum forces on the chassis 102 to receive, hold, and/or transfer the diaper pant 100. It is to be appreciated that each conveyance may include more than one conveyor, such as for example, multiple conveyors arranged in series along the machine direction and/or arranged in parallel along the cross direction. In addition, one or more of the conveyances can be configured as a rotating drum or vacuum drum. As discussed in more detail below, the conveyances 202, 204, 205 advance diaper pants 100 in a machine direction, MD, through a tucking zone 212, represented generally by a dashed line box in FIG. 4, wherein a side panel tucker pushes the side panels 104 and 106 into the chassis 102. And while the side panel tucker pushes the side panels 104 and 106 into the chassis 102, the vacuum forces exerted by the conveyances 202, 204, 205 on the chassis 102 are removed.

As shown in FIG. 4, diaper pants 100 are received between the first conveyance 202 and the second conveyance 204. It is to be appreciated that the diaper pants 100 may be subjected to various methods and apparatuses of assembly and construction before being received by conveyances 202, 204. Examples of such upstream processes and apparatuses are disclosed in U.S. Pat. Nos. 5,779,831; 6,036,805: 6,113,717; 6,497,032; 7,175,584; 7,322,925; and 7,335,150 and U.S. Patent Publication Nos. 2008/0083489A1; 2009/0098995A1; and 2009/0094941A1 all of which are incorporated herein by reference. As previously mentioned, the first conveyance 202 and second conveyance 204 may exert vacuum forces on the chassis 102 of the diaper pant 100 as the first and second conveyances 202, 204 advance the diaper pant in the machine direction, MD. For example, as shown in FIG. 4, the belts 206 of the first conveyance 202 and the second conveyance 204 exert opposing vacuum forces on the outer surfaces 134 of the first waist region 112 and the second waist region 114. The belts 206 of the first conveyance 202 and the second conveyance 204 may also diverge from each other along at least a portion of the machine direction length of the conveyance 204. Thus, as the chassis 102 advances along the machine direction, the opposing vacuum forces exerted on the first and second waist regions of the chassis pull and hold the inner surfaces 132 of the first and second waist regions 112, 114 apart from each other.

FIG. 5 shows a cross-sectional view of the diaper pant 100 and first and second conveyances 202, 204 of FIG. 4 taken along line 5-5. As shown in FIG. 5, the belt 206 of the first vacuum conveyance 202 includes a vacuum zone 214 that exerts a downward vacuum force on the outer surface 134 of the first waist region 112 of the chassis 102. And the belt 206 of the second vacuum conveyance 204 includes a vacuum zone 214 that exerts an upward vacuum force on the outer surface 134 of the second waist region 114 of the chassis 102. As such, the opposing forces exerted by the vacuum zones 214 on chassis 102 hold the inner surfaces 132 of the first and second waist regions 112 and 114 apart. In addition, the side panels 104 and 106 are shown in FIG. 5 in a relatively elongated and untucked configuration prior to the side panel tucker.

As shown in FIG. 5, the vacuum zones 214 of the first and second conveyances 202, 204 each define a lateral or cross directional, CD, width that may be less than the lateral width defined by the opposing longitudinal edges 120 and 122 of the chassis 102. In addition, the lateral or cross directional, CD, width of the vacuum zones 214 may also be less than the lateral width defined by the opposing longitudinal edges 146 and 148 of the absorbent core 142. However it is to be appreciated that the vacuum zones may be configured with different lateral widths and may define lateral widths that are larger or smaller than what is depicted. For example, some embodiments may include vacuum zones having lateral widths that are equal to or greater than the lateral widths of the absorbent core and/or chassis. In addition, the conveyances may also be configured with more than one vacuum zone along the cross direction CD and/or machine direction MD.

As previously mentioned with reference to FIG. 4, as the diaper pant 100 advances in the machine direction through the tucking zone 212 the opposing vacuum forces exerted by the first and second conveyance 202 and 204 are removed from the chassis. And with the vacuum forces removed from the chassis 102, a side panel tucker 216 pushes the side panels 104 and 106 into the chassis 102, such as shown for example in FIG. 6. As the side panels 104 and 106 are pushed into the chassis 102, the inner surfaces 132 of the first waist region 112 and the second waist region 114 move toward each other. Tucking the side panels 104 and 106 into the chassis 102 creates longitudinal fold lines 150 and 152 in the chassis 102. In the configuration shown in FIG. 6, the longitudinal fold lines 150 and 152 may also coincide with and may be defined by the longitudinal side edges 146 and 148 of the absorbent core 142. It is to be appreciated that the longitudinal fold lines 150 and 152 may be created in various different locations depending on the particular tucking method and configuration. For example, in some embodiments, the longitudinal fold lines may correspond with lateral side edges of the vacuum zones. In some embodiments, the side panels may not be completely tucked inside the chassis, and as such, the longitudinal fold lines may be defined along the lengths of the side panels.

It is to be appreciated that side panel tuckers 216 may be configured in various different ways. For example, as shown in FIG. 7, the side panel tuckers 216 are configured as rotating blades 218. As the diaper pant 100 advances in the machine direction past the side panel tuckers 216, a rotating blade or blades may impinge on each of the side panels 104 and 106 and push the side panels into the chassis 102. In another embodiment, shown in FIG. 8, the side panel tuckers 216 are configured as air jets 220. As the diaper pant 100 advances in the machine direction past the side panel tuckers 216, air discharged in the cross direction, CD, from the air jets 220 may impinge on each of the side panels 104 and 106 and push the side panels into the chassis 102. In yet other embodiments, the side panel tuckers 216 may be configured as rails that converge toward each other in the cross direction, CD. The side panel tuckers may be in contact with the absorbent article over the complete machine direction length between the vacuum zone or zones created by the first conveyance 202 and second conveyance 204 through the non-vacuum zone 212 to the vacuum zone or zones created by the first conveyance 202 and third conveyance 205. The side panel tuckers may be oriented in an overlapping orientation with one or more of the conveyances 202, 204 and 205 in the machine direction. Overlapping the side panel tucker and the conveyances 202 and 205 may help to maintain the side panels in a tucked position until the absorbent article is fully folded, i.e. interior surface 132 in the first waist region 112 is in contact with the interior surface 132 in the second waist region 114. In sill other embodiments, the side panel tuckers may be configured as one of the aforementioned devices that also discharges air to push the side panels into the chassis. For example, the side panel tuckers may be configured to discharge air from rotating blades, blades that travel on tracks, and/or converging rails. Other side panel tucker configurations are disclosed in U.S. Provisional Patent Application, entitled "Methods and Apparatuses for Tucking Side Panels of Absorbent Articles," and filed on Apr. 9, 2010, as well as U.S. Pat. Nos. 6,723,035 and 6,776,316, all incorporated herein by reference.

Referring back to FIG. 4, once the side panels 104 and 106 are pushed into the chassis 102, the diaper pant 100 may continue to advance on the first conveyance 202 in the machine direction. The waist regions 112, 114 of the diaper pant 100 may also be further compressed together to help hold the side panels 104 and 106 in the tucked position. For example, as shown in FIG. 4, after the tucking zone 212, the diaper pants 100 advance between the first conveyance 202 and the third conveyance 205. The belts 206 of the first conveyance 202 and the third conveyance 205 may be spaced closer together than the first conveyance 202 and second conveyance 204, or the belts 206 may converge toward each other as the diaper pant 100 travels in the machine direction.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for tucking first and second opposing side panels into a chassis of a diaper pant, the chassis including an inner surface and an outer surface, the chassis having longitudinally opposing first and second waist regions, longitudinally opposing first and second waist end edges disposed in the first and second waist regions, and a crotch region longitudinally intermediate of the first and second waist regions, the first and second side panels connecting the first waist region with the second waist region to form a waist opening and a pair of leg openings, the method comprising the steps of:

positioning the chassis on a conveyor having a vacuum zone;

applying a vacuum force from the vacuum zone to the first waist region of the chassis;

holding the first waist region of the chassis on the conveyor using the vacuum force from the vacuum zone;

advancing the chassis in a machine direction with the conveyor;

removing the vacuum force from the first waist region; and moving the inner surface of the chassis in the first waist region and the second waist region toward each other by pushing the first side panel and the second side panel laterally inward toward each other while the vacuum force is removed from the first waist region.

2. The method of claim 1, further comprising the step of applying a second vacuum force to one of the first waist region or the second waist region of the chassis after pushing the first side panel and the second side panel toward each other.

3. The method of claim 1, further comprising the step of:

applying a second vacuum force to one of the first waist region or the second waist region of the chassis after pushing the first side panel and the second side panel.

4. The method of claim 1, wherein the step of pushing the first side panel and the second side panel further comprises moving the first side panel in the machine direction along a first stationary rail and moving the second side panel in the machine direction along a second stationary rail.

5. The method of claim 4, wherein the step of pushing the first side panel and the second side panel further comprises discharging air from the first stationary rail against the first side panel and from second stationary rail against the second side panel.

6. The method of claim 1, wherein the step of pushing the first side panel and the second side panel further comprises moving the first side panel in the machine direction along a first rotating tucker blade and moving the second side panel in the machine direction along a second rotating tucker blade.

7. The method of claim 6, wherein the step of pushing the first side panel and the second side panel further comprises discharging air from the first rotating tucker blade against the first side panel and from second rotating tucker blade against the second side panel.

8. The method of claim 1, wherein the chassis further comprises an absorbent core having opposing longitudinal side edges defining a lateral width, and wherein the step of pushing the first side panel and the second side panel further comprises creating longitudinal folds in the chassis along the outer longitudinal edges of the absorbent core.

9. The method of claim 8, wherein the vacuum zone defines a lateral width that is smaller than the lateral width of the absorbent core.

10. The method of claim 1, wherein the first conveyor comprises an endless belt.

\* \* \* \* \*